United States Patent
Nelson et al.

(10) Patent No.: US 6,796,952 B2
(45) Date of Patent: Sep. 28, 2004

(54) KNEE BRACE SKIN PINCH GUARD

(75) Inventors: Kim Alex Nelson, Salt Lake City, UT (US); David B. Winer, Vista, CA (US)

(73) Assignee: DJ Orthopedics, LLC, Vista, CA (US)

( * ) Notice: Subject to any disclaimer, the term of this patent is extended or adjusted under 35 U.S.C. 154(b) by 60 days.

(21) Appl. No.: 09/945,114

(22) Filed: Aug. 31, 2001

(65) Prior Publication Data

US 2003/0045822 A1 Mar. 6, 2003

(51) Int. Cl.[7] .................................................. A61F 5/00
(52) U.S. Cl. .......................................... 602/26; 602/23
(58) Field of Search ............................. 602/23, 26, 27; 2/22, 24, 59, 60, 61, 62, 911, 241–242; 128/846, 882, 884; 36/127, 72 R, 132, 114, 136

(56) References Cited

U.S. PATENT DOCUMENTS 2,069,964 A * 2/1937 Miller
5,209,000 A * 5/1993 Rowland et al.
5,288,287 A 2/1994 Castillo et al.
5,634,211 A * 6/1997 Chen

FOREIGN PATENT DOCUMENTS

EP 0 014 124 A1 8/1980

* cited by examiner

Primary Examiner—Jerome W. Donnelly
(74) Attorney, Agent, or Firm—Knobbe, Martens Olson & Bear LLP

(57) ABSTRACT

A skin pinch guard is provided to prevent pinching of skin between a boot and the lower portion of a knee brace. The guard includes a pair of fasteners for removably attaching it to the lower cuff of the knee brace. The guard also preferably includes a plurality of fingers which extend into the boot so that the boot slides on the guard.

11 Claims, 3 Drawing Sheets

KNEE BRACE SKIN PINCH GUARD

BACKGROUND OF THE INVENTION

1. Field of the Invention

The present invention relates to medical devices and, in particular, to a knee brace pinch guard.

2. Description of the Related Art

Many types of braces have been made available for the support of body joints which have become weakened as a result of sports activity, accident, deterioration due to age, or disease. Braces for the knee are designed primarily to provide support while enabling the knee to function during normal activity.

Knee braces are often utilized by people who have suffered a knee injury and require some means of protection against further aggravation of the knee during rehabilitation. A knee brace can limit the amount of damage to an injured knee by providing the patient with adequate knee stabilization and control. Stabilization and control is achieved in such a manner as to permit the patient relative freedom in the normal use of the knee joint while, at the same time, permitting control over the joint so as to optimize healing.

In addition, knee braces are often employed by a person having previously suffered a knee injury who wishes to actively participate in strenuous and demanding physical activity. In such cases where the person seeks knee support in furtherance of activities involving heavy running or sprinting, it is extremely advantageous to design a knee brace which most accurately simulates the true motions of the anatomical knee joint. This will minimize the leg forces required to overcome mismatched motions and generally increase comfort levels.

Knee braces generally serve two purposes. Firstly, the brace has to support the knee at all times, but especially during movement. Secondly, the brace should limit knee movements in flexion or extension within limits beyond which injury to the knee may occur. Further, movements are limited within the varus/valgus plane.

Flexion is defined as flexing of the knee from the extended position to a position where the foot and ankle is bent towards the thigh. Extension is defined as being the opposite movement. An extended leg is normally straight with virtually no bending at the knee joint.

Knee braces for providing support for the knee of a person are well known in the art. Such braces generally include a tibial shell which is constructed so as to be closely configured to the shape of the lower leg and a femoral shell which is constructed so as to be closely configured to the shape of the thigh area of the leg. The two shells are secured to their respective areas on the leg and are interconnected by some type of mechanism so as to pivot relative to each other as the knee is bent. The mechanism is usually a pair of hinge joints, one on each side of the knee brace, with the tibial shell usually being attached to the lower part of each one of the two knee joints and the femoral shell usually being attached to the upper part of each one of the two hinge joints.

Often, skiers use knee braces to provide support while skiing downhill. When wearing knee braces equipped with a rigid posterior calf cuff, the skin between the top of the ski boot and the bottom of the calf cuff can become pinched, causing pain and discomfort for the skier.

Therefore, there is the need for a device for preventing the pinching of skin between a ski boot.

SUMMARY OF THE INVENTION

The present invention comprises a component for preventing the pinching of skin between a boot and a knee brace. A knee brace generally includes an upper portion and a lower portion having a rigid, inelastic upper cuff adapted to be secured to the thigh and a rigid, inelastic lower cuff adapted to be secured to the leg below the knee. The upper portion and lower portion each include a lateral arm and a medial arm, which are pivotally attached at a hinge, which permits rotation of the upper portion with respect to the lower portion. The knee brace also includes a plurality of adjustable straps for securing the knee brace to the leg. A skin pinch guard is also provided, removably attached to the lower portion to prevent skin of a user from being pinched between a boot and the lower portion.

The skin pinch guard generally includes a molded, rounded body and one or more fasteners integrally formed on the body. A plurality of fingers preferably extend from the body, which conform to the shape of the user's leg while providing relief from pinching. The guard removably attaches to the knee brace through the fasteners.

The fasteners may be tapered to provide a firm grip with the cuff. Alternatively, the fasteners may include a retention element for retaining or securely connecting the guard to the brace. The guard is preferably formed from an injection molded plastic material.

DETAILED DESCRIPTION OF THE PREFERRED EMBODIMENT

Knee Brace

Figure 1:
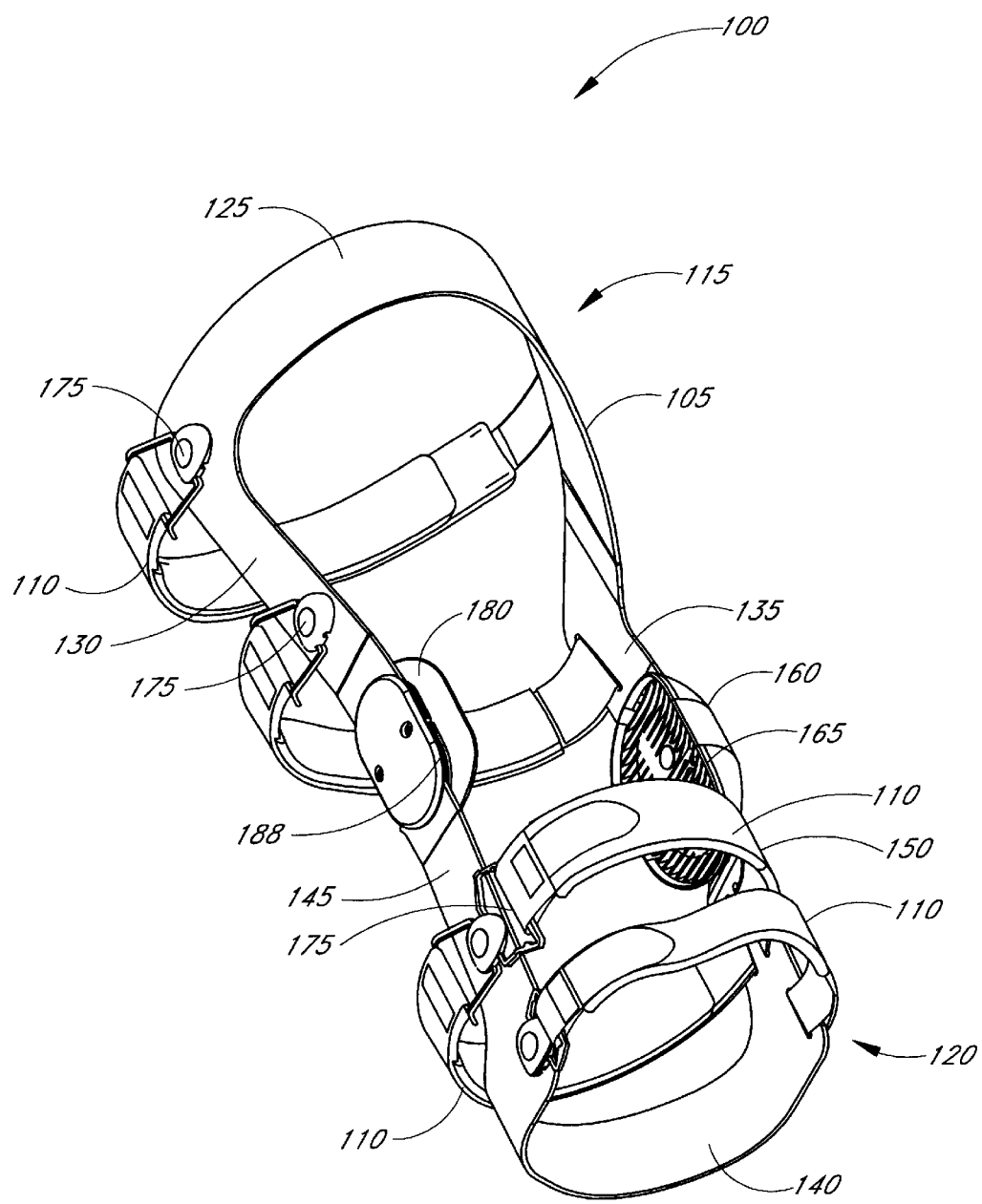
FIG. 1 is a perspective view of a knee brace of the present invention.
Figure 5:
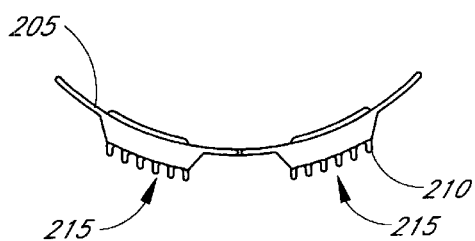
FIG. 5 is a top end view of the guard of FIG. 2.

FIG. 1 shows an orthopedic brace for supporting a joint having a plurality of compliant support components. The knee brace 100 of the present invention includes a hinged shell or frame 105 and a plurality of adjustable support straps 110 engaging the brace at two points on opposite sides of the hinge to stabilize the weakened joint throughout its range of motion. The shell 105 has an upper portion 115 conformable to the thigh and a lower portion 120 conformable to the lower leg. Each of the shell portions 115, 120 is preferably formed from a single continuous shaped piece of a stiff or rigid material such as certain plastics, fiberglass, composites, certain metals, and the like, as are known to those of skill in the art.

The upper portion 115 includes a cuff 125, having a lateral arm 130 and a medial arm 135. The cuff 125 has a preformed arcuate shape sized to snugly conformingly engage the anterior portion of the thigh.

The lower portion 120 includes a cuff 140, having a lateral arm 145 and a medial arm 150 extending therefrom. The lower portion 120 has substantially the same structure as the upper portion, but is sized to conform to the lower leg of the user. The lower cuff 140 has substantially the same configuration as the upper cuff 125, but the preformed arcuate shape thereof is sized somewhat smaller to snugly conformingly engage the calf of the lower leg.

The upper and lower portions 115, 120 are connected across rotatable hinges 155, 160. More specifically, lateral upper arm 130 is pivotally connected to lateral lower arm 145 and medial upper arm 135 is pivotally connected to medial lower arm 150 across lateral hinge 155 and medial hinge 160, respectively. A resilient pad 180 may also be provided to cushion the knee joint from the rigid hinges 155, 160.

Medial hinge 160 also preferably includes a hinge deflector 165 for preventing interference between medial hinges when a user is wearing a knee brace on each leg. The hinge deflector 165 acts as a shield to the internal components of the medial hinge 160 and deflects the opposite medial hinge, preventing the hinges from locking together.

The support straps 110 are preferably adjustable in length, enabling the user to modify the support strap tension, and consequently the degree of support the brace provides to the joint. Support straps 110 are preferably formed from a wear-resistant supple material such as pliant leather, or natural or synthetic cloth, such as nylon and the like. The material should be compliant, but substantially unstretchable.

Support straps 110 enable closure of brace 100 around the limb on which the brace is mounted. As seen in FIG. 1, each of the cuffs 125, 140 are held in place by straps. A separate strap is provided at the upper arms, surrounding the upper leg. A separate strap is provided at the lower arms, surrounding the lower leg. Each strap is integrally provided with a tab and cap fastener assembly 175 at the ends thereof to fix the strap and enable adjustment to the length of the straps 110 for close conformance of the shell 105 to the limb on which the brace is mounted.

Skin Pinch Guard

Referring to FIGS. 2–5, a skin pinch guard 200 includes a body 205 and a pair of fasteners 215, which permit easy attachment and removal of pinch guard 200 to and from lower cuff 140. Body 205 has a thin, relatively stiff shell-like configuration and is preferably, generally arcuate in cross-section to conform to a user's leg. A centrally located notch 202 provides some bendability for better conformance.

Figure 2:
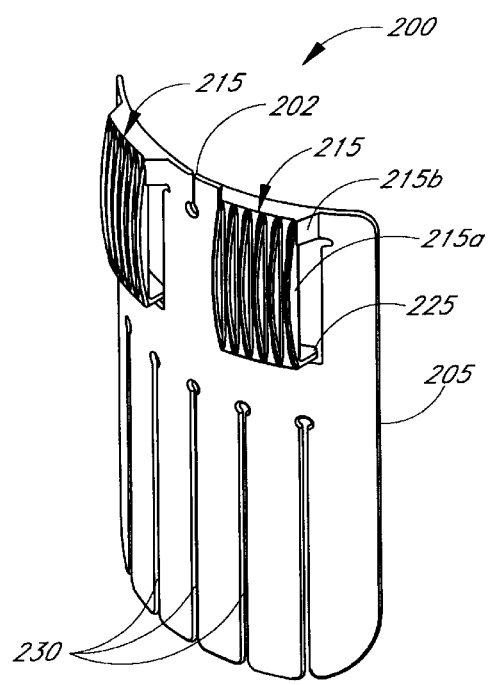
FIG. 2 is a perspective view of a knee brace pinch guard for use with the knee brace of FIG. 1.
Figure 4:
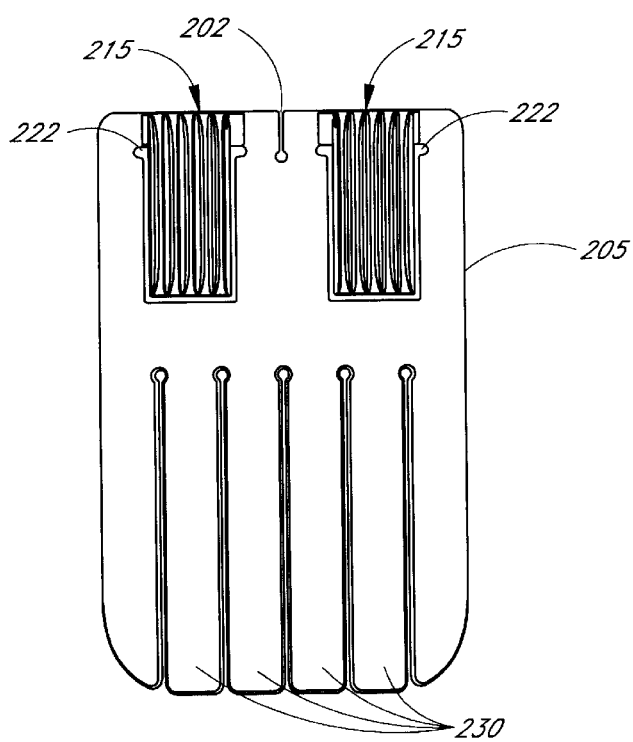
FIG. 4 is a front view of the guard of FIG. 2.
Figure 3:
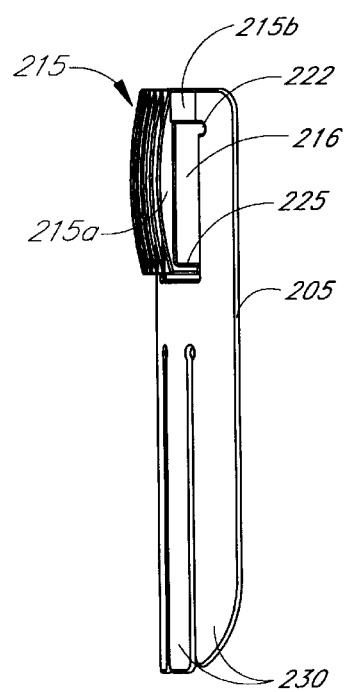
FIG. 3 is a side view of the guard of FIG. 2.
Figure 7:
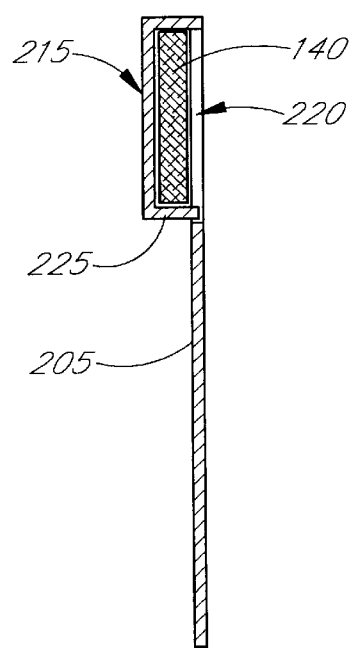
FIG. 7 is a detailed cross-sectional view of the knee brace and guard assembly on line 7—7 of FIG. 6.
Figure 8:
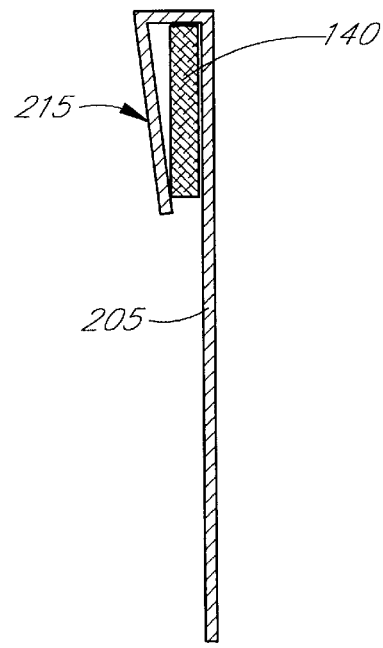
FIG. 8 is a detailed cross-sectional view of an alternative embodiment of a knee brace and guard assembly.

In the embodiment illustrated, each of the fasteners 215 is a generally rectangular element 215a that is attached at its upper end to the body 205 by a box-like shell or connector 215b. The shell spaces the element 215 a forwardly from the adjacent surface of the body 205. This creates a space 216 between the element and the otherwise forward face of the body 205. However, as can be seen in FIG. 7, there is actually an opening 220 in the body which is aligned with the fastener. Hence, the portion of the element 215a below the connector 215b is free to flex about the connector. Notches 222 in the edges of the opening 220 adjacent the connector 215b facilitate the flexing action. The element 215a may include an inwardly extending flange 225 on its lower end, as shown in FIGS. 2 and 3. The flange serves as a retention element for the skin guard 200 as explained below. In an alternative embodiment, the free end of the fastener may be tapered inwardly to serve as a retention element, as shown in FIG. 8.

The rear surface of the element 215a is preferably smooth and slightly curved consistent with the curvature of the body 205 and the cuff 140 of the knee brace. The front surface of the element 215a preferably has a plurality of spaced, strengthening ribs 210. As seen, the ribs are vertically oriented and tapered from a central higher area to lower ends.

The lower portion of the body 205 of pinch guard 200 beneath the fasteners 215 includes a plurality of fingers 230 that allow the pinch guard 200 to better conform to the shape of each user's leg while providing relief from pinching.

In a preferred embodiment, skin pinch guard 200 is formed from an injection molded plastic material, such as polypropylene. However, any material having sufficient rigidity and flexibility to provide relief from pinching is contemplated herein. As can be appreciated from the description, skin pinch guard 200 is an optional component of knee brace 100 and need not necessarily be included therewith.

Figure 6:
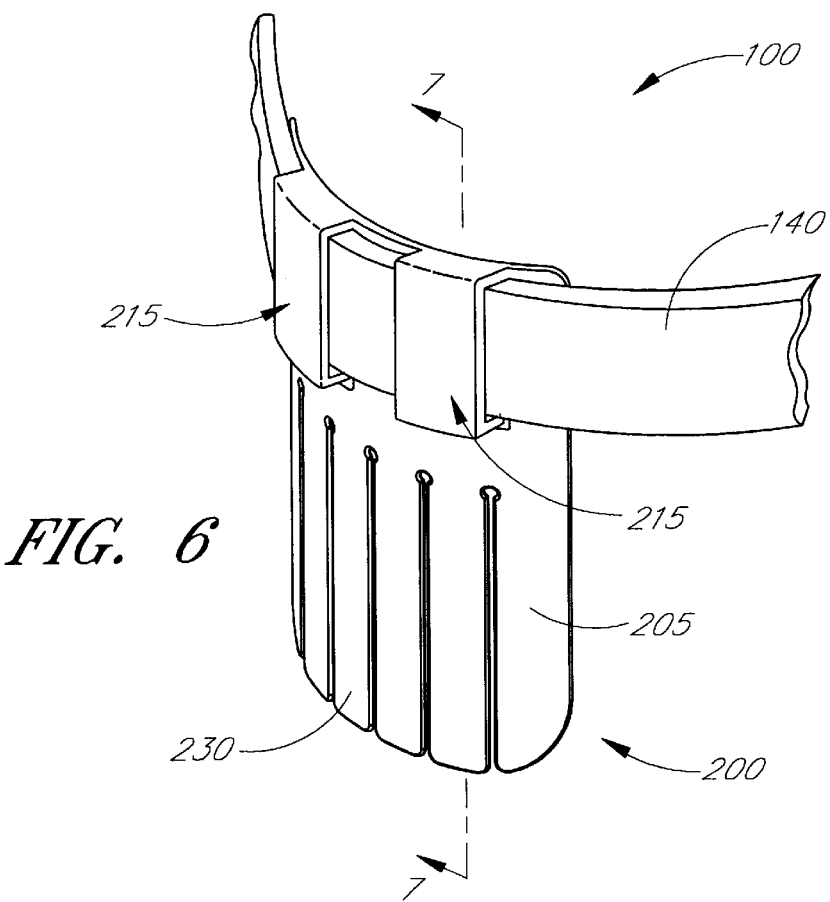
FIG. 6 is a perspective view of the knee brace and knee brace pinch guard assembly of the present invention.

FIG. 6 shows skin pinch guard 200 in use attached to knee brace 100. Fasteners 215 are removably attached to lower cuff 140 while fingers 230 are to extend into a ski boot. Fasteners 215 hook over cuff 140, such that body 205 is behind the knee brace 100, as viewed in FIG. 6, so that pinch guard 200 rests against the leg, with the fasteners 215 external of the knee brace cuff. FIG. 7 shows the attachment of fasteners 215 to cuff 140 using a retention element 225, in detail. In installation, the lower end of the fastener flexes outwardly and the cuff 140 slips into the space between the fastener and the body of the guard. FIG. 8 shows an alternative embodiment, wherein fasteners 215 are tapered to ensure securement of the fasteners to cuff 140.

Skin pinch guard 200 slides along the wearer's calf between the ski boot and the bottom of the proximal cuff 140 to prevent pinching. The fingers 230 extend down into the boot in a resting position. As the user flexes his leg, the boot slides up the body 205 along fingers 230. Hence, at one extreme, the tips of fingers 230 are within the boot, while at the other extreme, larger portions of the fingers 230 are within the boot. The ski boot slides with respect to guard 200 preventing skin from being pinched between the boot and cuff 140 of the knee brace. The user preferably wears the guard under the sock.

Although the device has been described with reference to ski boots, it is envisioned that the skin pinch guard may be used in any activity in which skin may become pinched between footwear and a knee brace.

Although the present invention has been described in terms of preferred embodiments, other embodiments of the invention including variations in dimensions, configuration and materials will be apparent to those of skill in the art in view of the disclosure herein. For example, various other techniques for securing the guard to the brace cuff include snaps, Velcro fasteners, rivets, screws, adhesive, etc. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A guard for preventing pinching of skin between a knee brace and a boot, comprising:

an arcuate relatively thin body, having a fastener integrally formed on an upper portion of said body and a plurality of depending fingers formed on a lower portion of said body;

wherein a portion of said fastener is raised from a forward face of said body to create a space between a back side of said fastener and said forward face of said body for receiving a portion of a knee brace cuff, said fingers and body being shaped to conform to the shape of a user's leg, said fingers being configured to provide relief from pinching by extending downward into a region between the user's leg and the boot.

2. The guard of claim 1, wherein said body is formed from an injection molded plastic material, and a tower end of said fastener is configured to retain said fastener connected to said brave.

3. A skin pinch guard for preventing pinching of skin between a brace and a boot, comprising:

a body configured to engage a calf of a person's leg; and at least one fastener for attaching an upper portion of said body to the knee brace, at least a portion of said fastener being raised from a forward face of said body for creating a space between a back side of said fastener and said forward face of said body, said fastener being adapted to extend around a cuff on the knee brace;

wherein said body has a lower portion configured to fit within an upper portion of the boot so that the guard prevents the skin from being pinched between the boot and the brace.

4. The guard of claim 1, wherein said fastener is attached to said body and said fastener is releasably securable to the brace.

5. The guard of claim 4, wherein said fastener has an upper portion attached to said body and a lower portion which is separated from said body and is configured to flex away from said body to permit said body to hook onto the cuff of a the knee brace.

6. The guard of claim 5, wherein said fastener is configured such that the upper portion of said body will fit between the knee brace and the person's skin while said fastener extends around the cuff of the knee brace.

7. The guard of claim 5, wherein said fastener, in combination with said body, creates a space for receiving the cuff of the knee brace.

8. The guard of claim 3, which includes a pair of said fasteners spaced apart from each other on an upper end of said body.

9. The guard of claim 3, wherein said lower portion of said body includes a plurality of flexible fingers.

10. The guard of claim 3, wherein said fastener includes a retention element on its lower end.

11. The guard of claim 3, wherein said fastener is oriented so that a lower free end of said fastener is self-biased into position to help retain said body on the knee brace.

* * * * *

UNITED STATES PATENT AND TRADEMARK OFFICE
CERTIFICATE OF CORRECTION

PATENT NO.     : 6,796,952 B2
DATED          : September 28, 2004
INVENTOR(S)    : Kim Alex Nelson and David B. Winer It is certified that error appears in the above-identified patent and that said Letters Patent is hereby corrected as shown below:

Column 5,
Line 6, delete "tower" and insert -- lower --;
Line 8, delete "brave" and insert -- brace --;
Line 10, after "between a" insert -- knee --; and Column 6,
Line 5, after "of" delete "a".

Signed and Sealed this

Seventh Day of February, 2006

JON W. DUDAS
*Director of the United States Patent and Trademark Office*